(12) United States Patent
Nielsen et al.

(10) Patent No.: US 10,702,560 B2
(45) Date of Patent: Jul. 7, 2020

(54) **ANTIBIOTIC SENSITIVE *BACILLUS* STRAINS HAVING ANTIMICROBIAL EFFECT AGAINST *E. COLI* AND *CLOSTRIDIUM PERFRINGENS* AND HAVING HIGH SPORULATION CAPACITY**

(71) Applicant: Chr. Hansen A/S, Hoersholm (DK)

(72) Inventors: Beatrice Nielsen, Hvidovre (DK); Mette Dines Cantor, Birkeroed (DK); Birgitte Stuer-Lauridsen, Virum (DK); Patrick Derkx, Tikoeb (DK); Eric Johansen, Hoersholm (DK)

(73) Assignee: CHR. HANSEN A/S, Hoersholm (DK)

(*) Notice: Subject to any disclaimer, the term of this patent is extended or adjusted under 35 U.S.C. 154(b) by 6 days.

(21) Appl. No.: 15/836,346

(22) Filed: Dec. 8, 2017

(65) Prior Publication Data

US 2018/0200309 A1 Jul. 19, 2018

Related U.S. Application Data

(62) Division of application No. 14/391,564, filed as application No. PCT/EP2013/057590 on Apr. 11, 2013, now Pat. No. 9,844,573.

(30) Foreign Application Priority Data

Apr. 13, 2012 (EP) .................... 12164087

(51) Int. Cl.

| A61K 35/742 | (2015.01) |
| A23K 10/18 | (2016.01) |
| C12R 1/07 | (2006.01) |
| C12R 1/125 | (2006.01) |
| C12N 1/20 | (2006.01) |
| C12N 15/01 | (2006.01) |

(52) U.S. Cl.
CPC ............ *A61K 35/742* (2013.01); *A23K 10/18* (2016.05); *C12N 1/20* (2013.01); *C12N 15/01* (2013.01); *C12R 1/07* (2013.01); *C12R 1/125* (2013.01)

(58) Field of Classification Search
CPC .......... C12R 1/07; C12R 1/125; A61K 35/742
See application file for complete search history.

(56) References Cited

FOREIGN PATENT DOCUMENTS

| WO | WO 2005/019417 A2 | 3/2005 |
| WO | WO 2010/033714 A1 | 3/2010 |

OTHER PUBLICATIONS

Barbosa et al., "Screening for *Bacillus* Isolates in the Broiler Gastrointestinal Tract," Applied and Environmental Miorobiciogy, vol. 71, No. 2, pp. 968-978, Feb. 2005.
Benitez et al., "Antimicrobial Activity of *Bacillus amyloliquefaciens* LBM 5006 is enhanced in the Presence of *Escherichia coli*," Curr Microbiol, No. 62, pp. 1017-1022, Nov. 2010.
Chaiyawan et al., "Characterization and probiotic properties of *Bacillus* strains isotated from broiler," The Thai Journal of Veterinary Medicine, vol. 40, No. 2, pp. 207-214, 2010.
Cutting, "*Bacillus* probiotics," Food Microbiology, No. 28, pp. 214-220, Mar. 2010.
European Food Safety Authority, "Update of the criteria used in the assessment of bacterial resistance to antibiotics of human or veterinary importance," The EFSA Journal, No. 732, pp. 1-15, Jun. 2008.
Guo et al. "Screening of *Bacillus* strains as potential probiotics and subsequent confirmation of the in vivo effectiveness of *Bacillus subtilis* MA139 in pigs," Antonie van Leewenhoek, vol. 90, pp. 139-146, Jul. 2006.
International Search Report dated Jun. 13, 2013 issued in PCT/EP2013/057590.
Klose et al., "In vitro antagonistic activities of animal intestinal strains against swine-associated pathogens," Veterinary Microbiology, No. 144, pp. 515-521, Feb. 2010.
López and Kolter, "Extracellular signals that define distinct and coexisting cell fates in *Bacillus subtilis*," FEMS Microbiol. Rev., No. 34, pp. 134-149. Dec. 2009.
Spiehs et al., "Effects of two direct-fed microbials on the ability of pigs to resist an infection with *Salmonelia enterica* serovar Typhimurium," Journal of Swine Health and Production, vol. 16, No. 1, pp. 27-36, Jan. 2008.

*Primary Examiner* — Ruth A Davis
(74) *Attorney, Agent, or Firm* — Foley & Lardner LLP (57) ABSTRACT

A *Bacillus* strain characterized by (i): sensitivity for ampicillin, vancomycin, gentamicin, kanamycin, streptomycin, erythromycin, clindamycin, tetracycline and chloramphenicol antimicrobial activity against *E. coli* and *Clostridium perfringens*; and (iii) a sporulation percentage of at least 80 when measured after 2 days of incubation. The invention further relates to a method for selecting such strains. Many of the identified strains according to the invention are of the species *Bacillus amyloliquefaciens*. Some of the *Bacillus amyloliquefaciens* were further identified as *Bacillus amyloliquefaciens* subsp. *amyloliquefaciens* whereas others were identified as *amyloliquefaciens* subsp. *plantarum*. A *Bacillus* strain of the invention may be used as a feed additive to animal feed where it has a probiotic effect.

20 Claims, 1 Drawing Sheet

Figure 1

ANTIBIOTIC SENSITIVE *BACILLUS* STRAINS HAVING ANTIMICROBIAL EFFECT AGAINST *E. COLI* AND *CLOSTRIDIUM PERFRINGENS* AND HAVING HIGH SPORULATION CAPACITY

CROSS REFERENCE TO RELATED APPLICATIONS

This application is a divisional of U.S. patent application Ser. No. 14/391,564, filed Oct. 9, 2014, which is the U.S. National Stage of International Application No. PCT/EP2013/057590, filed Apr. 11, 2013, which claims the benefit of European Patent Application No. 12164087.4, filed on Apr. 13, 2012.

FIELD OF THE INVENTION

*Bacillus* spp are used for probiotic solutions in the animal feed industry and positive effects of *Bacillus* based probiotics on production and health in production animals are well known (Spiehs et al., 2008; Cutting, 2011). Their usage is related to the ability of *Bacillus* to replace or reduce the use of antibiotics, which are used as growth promoters in the animal feed industry.

However, there is an unmet need for *Bacillus* strains which do not have antibiotic resistance against antibiotics which are commonly used for humans. The present invention provides isolated *Bacillus* strains which are characterized by sensitivity for ampicillin, vancomycin, gentamicin, kanamycin, streptomycin, erythromycin, clindamycin, tetracycline and chloramphenicol and which also have antimicrobial activity against major pathogens such as *E. coli* and *Clostridium perfringens*. The strains further have a sporulation percentage of at least 80 when measured on day 2 making it possible to efficiently produce safe and useful *Bacillus* spores for animal feed production.

The invention further relates to use of the spores of the *Bacillus* strains of the invention for production of animal feed additives, in particular products for pigs and poultry, where the strains have a probiotic (health, feed utilization and growth promoting) effect.

BACKGROUND OF THE INVENTION

Pigs, especially piglets, suffer from scours, that is, diarrhea, which can be caused by bacteria such as *Escherichia coli* (*E. coli*) and *Clostridium perfringens* Types A and C (*C. perfringens*). Scours can cause death losses and severe production losses, including weight loss, if left untreated.

*E. coli* is the primary cause for diarrhea in piglets and 50-75% of the antibiotic used on farms is used against weaning diarrhea, primarily caused by *E. coli*. Diarrhea is the biggest problem in weaners and growers (up to 40 kg) and *E. coli* is the most important pathogen causing diarrhea (Klose et al., 2010).

Enteric clostridial infections in swine occur predominantly in the preweaning period but are also associated with hemorrhagic bowel syndrome affecting pigs in the finishing period. Although immunization against *C. perfringens* type C has greatly reduced pre-weaning mortality, no commercial vaccines are currently available for *C. perfringens* type A. *C. perfringens* type A infections are now recognized with increasing frequency in preweaning pigs and approaches to diagnosis and prophylaxis are both different and more complex than those for type C infections.

Several infections and diseases in poultry are caused by pathogenic bacteria, including *E. coli* and *Clostridium perfringens*. Infections and diseases caused by pathogens result in increased mortality, decreased performance, and increased production costs. In addition, many of these pathogens can be transmitted to humans. Avian colibacillosis is a systemic infection caused by *E. coli* and occurs most commonly in young broilers and poults.

Probiotics are used in animal health applications in order to maintain healthy gut microflora, including a reduction in detrimental bacteria such as Clostridia and *E. coli* and an increase in beneficial bacteria such as *Lactobacillus* spp. and *Bifidobacterium*. Probiotics are well-suited to maintaining a healthy balance between pathogenic and beneficial bacteria because, unlike antibiotics, they do not destroy bacteria indiscriminately nor do they lead to antibiotic resistant strains of pathogenic bacteria. There are many mechanisms by which probiotics are thought to maintain healthy gut microflora: competitive exclusion of pathogenic bacteria, reduction of pathogenic bacteria through production of antimicrobial substances, enhancing growth and viability of beneficial gut microflora, and stimulating a systemic immune response in the animal.

In view of the foregoing, it would be desirable to have one or more *Bacillus* strains to treat or prevent diseases due to infections with *E. coli* and/or *Clostridium* in pigs and poultry.

Guo et al., 2006, describes screening of *Bacillus* strains as potential probiotics and a test of *Bacillus subtilis* MA139 in pigs. 124 samples were collected from broiler, pigs, soils, fermented foods and Chinese herbs. 750 aerobic spore-forming strains were isolated from these samples.

Inhibitory activity against *E. coli* K88 and K99, *Salmonella* and *Staphylococcus aureus* was tested using a disc plate diffusion assay. 6 Bacilli with best activity were tested for their survival within simulated GIT conditions (pH 2 and 0.3% bile salt). *B. subtilis* MA139 was the best candidate and was tested in vivo in piglets in a 28 days feeding trial with 90 piglets. ADG and feed utilization was improved. Lactic acid bacteria were increased, *E. coli* in feces was decreased. However, antimicrobial activity against *Clostridium perfringens* and sensitivity to antibiotics were not tested.

Barbosa et al., 2005 describes isolation of 237 *Bacillus* from feces from organically (contact to soil) reared broilers. 31 isolates were characterized. *B. subtilis* and *B. licheniformis* were among these. Several *B. subtilis* strains showed inhibition to *C. perfringens* and *S. aureus*. *B. licheniformis* also showed effect against *C. perfringens*. However, none of the selected *Bacillus* isolates exhibited antimicrobial activity against *E. coli* as defined in the present application. One selected *Bacillus* isolate shows reduction in growth intensity but not complete inhibition against *E. coli* strain O78:K80 and no effect against the other *E coli* strain tested (see Table 5). No data is provided on the sporulation percentage after 2 days of incubation or on the sensitivity to vancomycin, kanamycin, streptomycin, and clindamycin.

Chaiyawan et al., 2010, discloses a *Bacillus* strain sp. T3-1, which is susceptible to antibiotics widely used in medical treatment and which shows antimicrobial activity against *C. perfringens* ATCC 15191. The strain has no antimicrobial activity against *E. coli* O157. No data on the sporulation percentage after 2 days of incubation provided.

Benitez et al., 2011 has recently described that the presence of intact or inactivated *E. coli* enhanced the synthesis of antimicrobial peptides by *Bacillus amyloliquefaciens* LBM 5006 strain.

U.S. Pat. No. 7,754,469 relates to microorganisms and methods for treating poultry and U.S. Pat. No. 8,021,654 relates to methods of treating pigs with *Bacillus* strains.

However, in none of these articles or patents there is any description or suggestion to select for *Bacillus* strains that are sensitive for antibiotics which are commonly used for humans, have antimicrobial activity against both *Clostridium perfringens* and *E. coli* and have a high sporulation percentage in order to make the strain useful for efficient sporulation and thus *Bacillus* probiotic production.

None of the prior art documents e.g. Barbosa et al., 2005, Chaiyawan et al., 2010, and Guo et al., 2006 disclose strains having sensitivity for antibiotics which are commonly used for humans, antimicrobial activity in the sense of inhibition of growth against both *Clostridium perfringens* and *E. coli*, and a high sporulation percentage.

In summary, the prior art relating to screening of *Bacillus* strains does not provide the three distinguishing features of the present invention, i.e. sensitivity for antibiotics which are commonly used for humans, antimicrobial activity against *E. coli* and *Clostridium perfringens* and a high sporulation percentage. Nor does the prior art provide *Bacillus* strains fulfilling these three criteria.

SUMMARY OF THE INVENTION

The problem to be solved by the present invention is to provide a *Bacillus* strain, which is characterized by sensitivity for ampicillin, vancomycin, gentamicin, kanamycin, streptomycin, erythromycin, clindamycin, tetracycline and chloramphenicol; antimicrobial activity against *E. coli* and *Clostridium perfringens*; and a sporulation percentage of at least 80 when measured on day 2.

The solution is based on a selection method developed by the present inventors for the identification of improved *Bacillus* strains having these improved properties.

A first essential step of the selection method is to specifically screen for *Bacillus* strains which are sensitive towards the antibiotics which are commonly used for humans. More specifically, the strains are screened for sensitivity for ampicillin, vancomycin, gentamicin, kanamycin, streptomycin, erythromycin, clindamycin, tetracycline and chloramphenicol.

Further, the strains are screened for antimicrobial activity against *E. coli* and *Clostridium perfringens* and for having a sporulation percentage of at least 80 when measured on day 2.

Out of 261 isolates from soil and feces and food sources investigated by the present inventors, 161 isolates were antibiotic resistant in the pre-screening test described in the examples. Of the 100 isolates that were sensitive to antibiotics 56 had antimicrobial effect against *Clostridium perfringens* and only 22 had effect against both *E. coli* and *Clostridium perfringens*. Of these were 12 isolates from the species *B. amyloliquefaciens*. Other representative strains were from the species *B. subtilis* and *B. mojavensis*. Tables 2 and 3 summarize the results of Chr. Hansen proprietory strains (22 of the 32 strains selected for the secondary screening).

The selection process focused on (i) safety, (ii) effect and (iii) high sporulation in media suitable for production. The safety aspect is mainly based on the absence of antibiotic resistance that is important due to the increased cases of resistant bacteria in human. These bacteria have resulted in well known diseases that no longer can be treated with antibiotics as the pathogen bacteria have become resistant.

It is well known that *Bacillus* can produce substances that may have antimicrobial activity as i.e. bacteriocins, bacteriolytic enzymes or surfactins. The second selection criterium, effect against *E. coli* and *Clostridium perfringens*, is important as both pathogens are main causes for diarrhea in pigs and poultry. The effect is tested against three strains of *E. coli* and against *Clostridium perfringens* type A, but it is contemplated that the results are indicative for a general effect against *E. coli* and for an effect against also other types of *Clostridia* such as *Clostridium perfringens* type C.

The third selection criterion is important for the production of the probiotic. The production process takes place in fermentors growing the *Bacillus* and at the end of the process a high sporulation rate is needed for a high production efficacy. The sporulation process of *Bacillus* has been investigated for many years but there are still a lot of questions. It is thus well known among persons of skill in the art working with the production and process development of *Bacillus* that some *Bacillus* strains have a very low sporulation rate. It has been suggested that *Bacillus* differentiates into subpopulations of specialized cells as i.e. communities that sporulate, communities that produce enzymes for the degradation of complex nutrients and communities that die (Lopez and Kolter, 2010). This differentiation seems to be regulated by extracellular signals, most of these produced by the *Bacillus* itself. It has thus been hypothesized that a high production of enzymes or antimicrobial substances may result in a low sporulation efficacy. For the person of ordinary skill in the art it is thus unusual and surprising for a *Bacillus* strain to have both an antimicrobial activity and a high sporulation percentage.

DETAILED DESCRIPTION OF THE INVENTION

Figure 1:
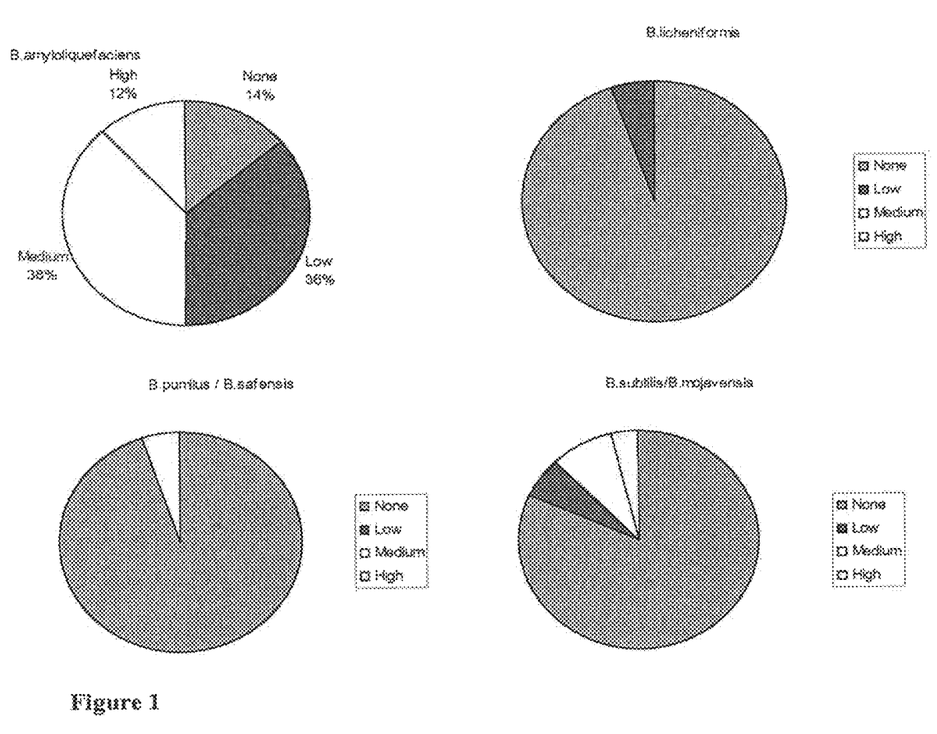
FIG. 1 shows schematically the antimicrobial activity of 261 Bacilli strains. It is surprising that many *Bacillus amyloliquefaciens* strains have antimicrobial effect.

The phase-out of antibiotic growth promoters in the European Union in 2006 has resulted in an increased need for cost-effective feed additives with high efficacy and thus the need for new probiotics. *Bacillus*-based probiotic feed additives are known for their positive effects on health and production in pigs and poultry. These products are relevant for the feed industry because spores are heat stable and can survive the pelletizing process at temperatures up to 90-95° C.

Probiotics for pigs need to be safe for animals, humans and the environment and should increase growth and feed utilization of the animal. The objective of the present invention was to screen in three steps a wide range of aerobic endosporeforming bacteria (AEB) from different sources for their probiotic effect in pigs. The AEB were isolated from fermented food (Kantong, and Gergoush primary starters), pig feces, soil and different culture collections. 261 AEB isolates were identified by sequencing of 16S rDNA genes, and investigated for relevant antibiotic resistance by determination of the minimal inhibitory concentration (MIC) of several relevant antibiotics.

Further analyses included bile and acid tolerance, pathogen inhibition, growth in different media, sporulation as well as interactions with animal cell lines to assess the likelihood of positive effects on tight junctions in the intestinal system. Results show a high difference between both species and strains. The isolated species were primarily of the genus *Bacillus* including *B. amyloliquefaciens*, *B. subtilis* and *B. safensis* from food sources, *B. subtilis*, *B. pumilus*, *B. amyloliquefaciens*, *B. licheniformis*, *B. megaterium* from feces and *B. licheniformis* and *B. simplex* from soil.

Many of the isolates showed undesirable antibiotic resistance above breakpoints defined by EFSA and were discarded due to safety concerns. Good growth was observed for most of the strains when grown overnight in veal infusion broth, whereas 16% had unsatisfactory growth in a medium suitable for fermentation. In step 2 of the screening process, 32 selected strains with no antibiotic resistance were identified by sequencing the gyrB gene, and PFGE fingerprinting. In addition, their antimicrobial effect on selected pathogens was tested and considerable variation was observed between isolates. Several of the isolates showed inhibition of *Clostridium perfringens* while only a few isolates inhibited *E. coli*. The results of the present invention thus confirm that inhibition of growth of both *Clostridium perfringens* and *E. coli* is only rarely combined. Step 3 of the screening process involved 10 strains with high pathogen inhibition and included determination of the heat stability of spores, genome sequencing and further in vitro studies showing their effect on tight junctions.

The present invention provides *Bacillus* strains characterized by (i) sensitivity for ampicillin, vancomycin, gentamicin, kanamycin, streptomycin, erythromycin, clindamycin, tetracycline and chloramphenicol.

By the term "sensitivity for ampicillin, vancomycin, gentamicin, kanamycin, streptomycin, erythromycin, clindamycin, tetracycline and chloramphenicol" is meant that a strain, to be considered as sensitive to a particular antibiotic, must not grow at the breakpoint level given by EFSA (EFSA, 2008) outlined in Table 1.

The MIC values outlined in Table 1 are based upon the guidelines issued by EFSA (Technical guidance prepared by the Panel on Additives and Products or Substances used in Animal Feed (FEEDAP) on the update of the criteria used in the assessment of bacterial resistance to antibiotics of human and veterinary importance. The *EFSA Journal* (2008) 732, 1-15) provides a list of antibiotics and acceptable cut-off values for the genus *Bacillus*. There is no breakpoint given by EFSA for ampicillin for *Bacillus*, however a breakpoint exist for several other bacteria, i.e. *Lactobacillus* spp. Thus this sensitivity of *Bacillus* strains against ampicillin has been chosen as a breakpoint for the present invention.

TABLE 1

EFSA breakpoints for various antibiotics commonly used for humans

| Antibiotic type | Antibiotic | EFSA breakpoint mg/L |
| --- | --- | --- |
| B-lactam | Ampicillin | 4 |
| Glycopeptide | Vancomycin | 4 |
| Aminoglycosides | Gentamicin | 4 |
| | Kanamycin | 8 |
| | Streptomycin | 8 |
| Macrolide | Erythromycin | 4 |
| Lincosamide | Clindamycin | 4 |
| Tetracycline | Tetracycline | 8 |
| Chloramphenicol | Chloramphenicol | 8 |

To be within the scope of the present invention the strain has to be sensitive towards all of the above antibiotics. In practice this means that no growth of the strain is observed at the breakpoint level when tested by a microdilution method (minimum inhibitory concentration (MIC)).

According to the present invention the MIC is measured by a broth microdilution method as outlined by the standard of CLSI (Clinical and Laboratory Standards Institute M07-A8 and M45-A2) performed as follows:

A suspension of an over-night growth of the strain to be tested is inoculated in ISO-SENSITEST Broth (Oxoid CM0473) in microtitre plates at an approximate concentration of $10^5$ cfu/ml (colony-forming units/ml) in two-fold serial dilutions of the antibiotic to be tested (total volume 100 μl/well) and incubated aerobically for 20-24 hours at 37° C. The pre-fabricated panels VetMIC Lact-1 & Lact-2 comprising the antibiotics ampicillin, vancomycin, gentamicin, kanamycin, streptomycin, erythromycin, clindamycin, tetracycline, and chloramphenicol can be used. The results are recorded after 24 hours as the lowest concentration of the antibiotic to inhibit visible growth.

The first part of aspect (ii) of the invention relates to a *Bacillus* strain which exhibits antimicrobial activity against *E. coli*. According to the present invention this is measured by the *E. coli* agar spot test performed as follows:

9 ml of Veal Infusion Broth (VIB) is inoculated with the *Bacillus* culture to be tested and incubated at 37° C. and 175 rpm overnight. Concurrently, 9 ml of Brain Heart Infusion (BHI) broth is inoculated with an *E. coli* strain selected from *E. coli* O149 (O149:k91,k88a), *E. coli* O147 (O147:K89 F4), and *E. coli* O101 (O101, F5) and incubated overnight at 37° C.

Overnight cultures of *E. coli* are added in a volume of 2 ml each into 200 ml liquid VIB agar at 50° C., and poured into each bioassay dish. Dishes are dried in a sterile bench. The overnight *Bacillus* culture to be tested is spotted onto the surface of the VIB agar mixed with *E. coli* and incubated at 37° C. for 2 days. Radii of the inhibition zones around the spots and spots diameters are recorded.

A *Bacillus* strain is considered to exhibit an antimicrobial activity towards *E. coli* if the inhibition zone is at least 1.5 mm. Preferably, the inhibition zone is at least 2.0 mm, such as at least 2.5 mm, more preferably at least 3 mm, most preferably at least 3.5 mm and even more preferably at least 4 mm. The inhibition zone may be different for the various *E. coli* strains. For a strain to be considered to exhibit an antimicrobial activity against *E. coli* according to the present invention it should exhibit an inhibition zone of at least 1.5 mm for all of the *E. coli* strains tested. Preferably, the inhibition zone of two or even more preferably the inhibition zone of all three of the *E. coli* strains is at least 2 mm. A *Bacillus* strain of the invention is characterized by inhibition of growth of *E. coli*, in particular inhibition of growth of the tested species. As evidenced by the prior art and confirmed by the present inventors, no inhibition of growth of one *E. coli* species is often combined with no inhibition of growth of another *E. coli* species (Table 5, Barbosa et al., 2005) and vice versa, i.e. inhibitory activity of one *E. coli* species is often combined with inhibitory activity of other *E. coli* species (Table 1, Guo et al., 2006).

The second part of aspect (ii) of the invention relates to a *Bacillus* strain which exhibits antimicrobial activity against *Clostridium perfringens*. According to the present invention this is measured by the *Clostridium perfringens* agar spot test performed as follows:

9 ml of VIB is inoculated with the *Bacillus* culture to be tested and incubated at 37° C. and 175 rpm overnight. Concurrently, 9 ml of BHI broth is inoculated with *Clostridium perfringens* Type A, DSM 756, and incubated overnight at 37° C. in an anaerobic jar.

Bacillus cultures are spotted onto the surface of the VIB agar in petri dishes and incubated at 37° C. overnight. *C. perfringens* overnight culture in a volume of 2 ml is mixed with 200 ml liquid BHI agar, and poured onto VIB agar with grown *Bacillus* spots. The dishes are incubated anaerobically at 37° C. for 1 day. Radii of clarified inhibition zones round the spots are measured.

A *Bacillus* strain is considered to exhibit an antimicrobial activity towards *Clostridium perfringens* if the inhibition zone is at least 5 mm. Preferably, the inhibition zone is at least 6 mm, more preferably at least 7 mm. A *Bacillus* strain of the invention is characterized by inhibition of growth of *Clostridium perfringens*, in particular inhibition of growth of the tested species. As known by the person of skill in the art, no inhibition of growth of one species is often combined with no inhibition of growth of other *Clostridium perfringens* species and vice versa, i.e. inhibition of growth of one *Clostridium perfringens* species is often combined with inhibition of growth of other *Clostridium perfringens* species.

*Bacillus* cells exist as bacillus spore cells and bacillus vegetative cells. When reference is made herein to *Bacillus* cells, this relates to both.

The term "*Bacillus* spore" in relation to a *Bacillus* spore cell relates herein to a spore that according to the art may be characterized as a dormant, tough, non-reproductive structure produced by *Bacillus* bacteria. The primary function of spores is generally to ensure the survival of a bacterium through periods of environmental stress. They are therefore resistant to ultraviolet and gamma radiation, desiccation, lysozyme, temperature, starvation, and chemical disinfectants. Spores are commonly found in soil and water, where they may survive for long periods of time. The spore coat is impermeable to many toxic molecules and may also contain enzymes that are involved in germination. The core has normal cell structures, such as DNA and ribosomes, but is metabolically inactive. When a bacterium detects that environmental conditions are becoming unfavorable it may start the process of sporulation, which takes about eight hours.

The term "*Bacillus* vegetative cell" relates to functional vegetative *Bacillus* cells, which can divide to produce more vegetative cells.

In aspect (iii), the invention relates to a *Bacillus* strain which exhibits a sporulation percentage of at least 80 when measured on day 2. According to the present invention, the sporulation percentage is assayed as follows:

A *Bacillus* strain to be tested is added in a volume of 50 μl into 700 μl VIB in a Deep well (DW) plate and incubated at 37° C. and 175 rpm overnight. The *Bacillus* overnight culture in a volume of 50 μl is transferred to 700 μl of a sporulation medium comprising (w/w) 95% water; 1.5% nitrogen source (i.e. yeast); 3% sucrose; 0.06% microminerals; dipotassiumhydrogenphosphate 0.1% in DW plates. The plate is incubated at 37° C. and 175 rpm for 3 days. Sporulation is followed microscopically and spore percentage (number of spores compared to the total number of *Bacillus* cells) is determined by visual evaluation after 1 day (24 hours), 2 days (48 hours) and 3 days (72 hours) of incubation. By the term "having a sporulation percentage of at least 80 when measured on day 2" is meant that at least 80% of the cells have sporulated after 2 days of incubation. The sporulation percentage may preferably be higher such as at least 85%, at least 90%, at least 95% or at least 99%. An important object of the present invention is to select for *Bacillus* strains having cells with a high sporulation percentage in order to make the strain useful for animal feed production. A high sporulation percentage which may also be termed a high sporulation rate is needed for a high production efficacy as described above.

As described above, the prior art has described methods for selecting *Bacillus* strains, but the prior art screening methods have not focused on the sporulation percentage. Accordingly, the prior art selected *Bacillus* strains are not likely to sporulate to a sufficient degree to comply with the sporulation percentage as described herein.

Three strains having the combined ability of high growth properties and sporulation, no antibiotic resistance and high antimicrobial activity have been selected and deposited. But also other strains, in particular strains of the species *Bacillus amyloliquefaciens* (see strains D-J in Tables 2 and 3) fulfil the criteria outlined in the claims and thus included within the scope of the present invention.

As evident from FIG. 1 in particular many strains of the species *Bacillus amyloliquefaciens* are within the scope of the present invention. It is surprising that many *Bacillus amyloliquefaciens* strains have antimicrobial effect, as it has been assumed up to date that antimicrobial effect of the genus *Bacillus* is strain-specific and not related to species.

Based on the detailed assay descriptions the person of ordinary skill in the art is able to repeat these assays to determine whether a specific *Bacillus* strain complies with the sensitivity of item (i), the antimicrobial activity of item (ii) and the sporulation percentage of item (iii) of the various aspects of the invention. In this manner the person of ordinary skill in the art will be able to consistently produce strains with the stated properties. Preferably, the selection method will also include (iv) assaying for sensitivity of the vegetative cells at pH 4, and (v) assaying for bile resistance to ensure that the strains are able to survive to a sufficient degree in the gastrointestinal tract. Evidently, these assays can be performed in any order and some strains may be excluded during the process if they do not fulfill the criteria.

It is known from the literature that bile has some negative influences on the survival and germination and outgrowth of bacillus spore cells to vegetative cells in the GIT of animals. Therefore probiotic bacteria shall generally be able to survive and proliferate in the gut of animals by being able to tolerate a low pH and resistant to bile salt in order to be useful as probiotic bacillus compositions for the addition to animal feed. The examples provide useful in vitro tests in this regard. The test for sensitivity to low pH (simulating gastric conditions) focuses on the resistance of vegetative cells to pH 4. It is well known that spores are resistant at pH values of 2-3 and that vegetative cells will die at pH 2. However, gastric pH may have pH values of up to 4 especially in feeding conditions. This may result in germination of the spores and it is thus relevant to test the sensitivity of vegetative cells at pH 4. Selected strains should preferably be resistant to pH at 4. Results for selected strains are presented in Table 2.

The strain of the invention is of the genus *Bacillus*, preferably one of the species *Bacillus amyloliquefaciens,* such as *Bacillus amyloliquefaciens* subsp. *amyloliquefaciens* or *Bacillus amyloliquefaciens* subsp. *plantarum, Bacillus simplex, Bacillus licheniformis, Bacillus megaterium, Bacillus mojavensis, Bacillus pumilus, Bacillus safensis, Bacillus simplex, Bacillus subtilis, Bacillus atrophaeus, Bacillus methylotrophicus, Bacillus siamensis, Bacillus vallismortis* or *Bacillus tequilensis.*

The initial method of identification of the 261 strains was based on 16S. This method cannot distinguish between some closely related species of *Bacillus*. Thus, a strain may be identified as related to the group consisting of the species *Bacillus amyloliquefaciens/atrophaeus/methylotrophicus/* siamensis/vallismortis or the group consisting of the species *Bacillus mojavensis/subtilis/tequilensis*. Both groups contain many strains which fulfill the criteria of the invention and these groups thus represent important embodiments of the invention.

Where considered appropriate, the strains were further identified by a more detailed method (gyr B)). The data shown in Tables 2 and 3 are primarily based on *Bacillus amyloliquefaciens* (identified by gyr B). Selected *Bacillus amyloliquefaciens* isolates were further identified by RNA polymerase beta subunit (rpo B) gene sequence analysis and the subspecies identified and presented in Tables 4, 5 and 6.

It is desirable that the strain exhibits heat stability. Results for selected strains are presented in Table 4. The heat stability at 99.5° C. is measured in cfu as reduction after 2, 5 and 10 min in relation to time 0 (log/log). A reduction below 2 is achieved with common commercial *Bacillus* spore formulations. For strains within the scope of the present invention the reduction should preferably be 0.5 or less after 2 min, more preferably 0.25 or less, most preferably 0.05 or less. In preferred embodiments the reduction after 5 min should preferably be 2.5 or less, more preferably 1 or less, most preferably 0.5 or less and after 10 min the reduction should also preferably be 2.5 or less, more preferably 1 or less, most preferably 0.5 or less. All of the strains in the table exhibit an appropriate heat stability. As evident from the table strains B, D and F have a very high heat stability even after 10 min. It is noteworthy that both B and F are *Bacillus amyloliquefaciens* subsp. *amyloliquefaciens* strains making this subspecies a preferred embodiment of the present invention.

Enzyme production has been investigated in Example 4. The present findings show for all investigated strain a cellulase activity of 50 mU/ml or more. It is contemplated that such an activity will be a beneficial property for a *Baccillus* strain of the invention. For certain embodiment it may be preferred that the strain has an even higher cellulase activity, such as 100 mU/ml or more, as found for the *B. amyloliquefaciens* subsp. *plantarum* strains making this subspecies a preferred embodiment of the present invention. For strains within the scope of the present invention the cellulase activity should preferably be 50 mU/ml or more, more preferably 100 mU/ml or more, most preferably 250 mU/ml or more, even more preferably 400 mU/ml or more.

Some strains show a high xylanase activity of 70 mU/ml or more. Table 5 shows that for the investigated strains high cellulase activity is not necessarily combined with high xylanase or high protease activity defined as 40000 RFU/OD or more. Strains G, I and J which are all *B. amyloliquefaciens* subsp. *plantarum* are examples of strains demonstrating high activity for all three enzymes.

In a preferred embodiment the *Bacillus* strain is a *Bacillus subtilis*, a *Bacillus mojavensis* or a *Bacillus amyloliquefaciens*. Most preferably, the strain is selected from the group consisting of (a) the *Bacillus mojavensis* strain with accession number DSM 25839; (b) the *Bacillus amyloliquefaciens* strains with accession number DSM 25840, accession number DSM 27032 or accession number DSM 27033, and (c) the *Bacillus subtilis* strain with accession number DSM 25841; and mutant strains thereof.

Another aspect of the invention relates to a method for obtaining a mutant strain of
(a) the *Bacillus mojavensis* strain with accession number DSM 25839;
(b) the *Bacillus amyloliquefaciens* strains with accession number DSM 25840, accession number DSM 27032 or accession number DSM 27033; or
(c) the *Bacillus subtilis* strain with accession number DSM 25841;

the method comprising optionally subjecting the strain to mutagenization treatment and selecting for mutant strains having the following properties
(i): sensitivity for ampicillin, vancomycin, gentamicin, kanamycin, streptomycin, erythromycin, clindamycin, tetracycline and chloramphenicol;
(ii) antimicrobial activity against *E. coli* and *Clostridium perfringens*, and
(iii) a sporulation percentage of at least 80 when measured on day 2.

The strain may be subjected to a mutagenization treatment as described in further detail below to obtain mutant strains and afterwards a selection process is performed. Alternatively, a selection is performed for spontaneously occurring mutants.

The method for obtaining a mutant strain may also include (iv) assaying for sensitivity of the vegetative cells at pH 4, and (v) assaying for bile resistance to ensure that the strains are able to survive to a sufficient degree in the gastrointestinal tract. Evidently, these assays can be performed in any order and some strains may be excluded during the process if they do not fulfill the criteria.

A bacterial "strain" as used herein refers to a bacterium which remains genetically unchanged when grown or multiplied. The multiplicity of identical bacteria are included.

"Wild type strain" refers to the non-mutated form of a bacterium, as found in nature.

A "mutant bacterium" or a "mutant strain" refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with any conventionally used mutagenization treatment including treatment with chemical mutagens, such as a chemical mutagen selected from (i) a mutagen that associates with or become incorporated into DNA such as a base analogue, e.g. 2-aminopurine or an interchelating agent such as ICR-191, (ii) a mutagen that reacts with the DNA including alkylating agents such as nitrosoguanidine or hydroxylamine, or ethane methyl sulphonate (EMS) or N-methyl-N'-nitro-N-nitroguanidine (NTG), UV- or gamma radiation etc. In contrast, a "spontaneous mutant" or "naturally occurring mutant" has not been mutagenized by man.

A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

Mutant bacteria as described above are non-GMO, i.e. not modified by recombinant DNA technology. As an alternative to above preferred method of providing the mutant by random mutagenesis, it is also possible to provide such a mutant by site-directed mutagenesis, e.g. by using appropriately designed PCR techniques or by using a transposable element which is integratable in bacterial replicons.

When the mutant is provided as a spontaneously occurring mutant the above wild-type strain is subjected to the selection step without any preceding mutagenization treatment.

Several species of *Bacillus* have GRAS status, i.e., they are generally recognized as safe. All *B. subtilis* strains are GRAS. The *Bacillus* strains described herein are aerobic and facultative spore formers. *Bacillus* species are the only spore formers that are considered GRAS. Feeding microorganisms that have GRAS status to livestock is an acceptable practice amongst producers, veterinarians, and others in the livestock industry.

Accordingly, in a further aspect the invention relates to a *Bacillus* composition comprising cells of a *Bacillus* strain of the invention. The composition may comprise cells of at least one, at least two, at least three, at least four or even more *Bacillus* strains chosen from at least one of the strains of the invention. Preferably, the cells of the *Bacillus* composition are spore cells.

The relevant *Bacillus* strains of the composition may be present in a commercially relevant form known to the skilled person. Accordingly, in an embodiment the *Bacillus* strains of the composition are present as dried (e.g. spray dried) cells or as frozen cells. The composition may be provided in any suitable form such as in the form of a liquid, a slurry, a powder or a pellet.

In a preferred embodiment the *Bacillus* composition comprises from $10^5$ to $10^{12}$ CFU/g, more preferably from $10^6$ to $10^{12}$ CFU/g, and most preferably from $10^7$ to $10^{12}$ CFU/g.

The term "CFU/g" relates to the gram weight of the composition as such, including suitable relevant additives present in the composition. As known to the skilled person a commercially relevant bacterial composition generally also comprises other relevant additives such as e.g. one carrier/ingredient of the group belonging to whey, whey permeate, calcium carbonate/limestone and anti caking agents such as aluminum silicates and kieselgur (diatomaceous earth). It does not include the weight of a suitable container used to package the *Bacillus* composition. An embodiment relates to a composition packaged into a suitable container.

Compositions of the present invention may include a *Bacillus* strain of the invention including mutants, and carriers that make these compositions suitable for feeding to animals as a feed additive or as an additive for drinking water. Alternatively, the *Bacillus* strain of the invention including mutants may be formulated with animal feed ingredients, including feed protein and/or feed carbohydrates. Such combinations may be in the form of pellets that are extruded through standard pelleting processes.

The *Bacillus* composition as described herein may be used as a probiotic additive to animal feed. The invention also provides a method for producing an animal feed or premix comprising adding a *Bacillus* composition of the invention to an animal feed.

As used herein the term "premix" refers to a *Bacillus* strain added to a carrier to make a premix which is then added to the feed at a desired inclusion rate and fed to the animal.

Another aspect of the invention relates to a method for feeding an animal comprising administering a *Bacillus* composition of the invention or an animal feed or premix produced according to the invention to an animal.

Example 5 describes feeding trials with strains B and C and shows that both *Bacillus* strains probiotic products supplemented to nursery diets numerically improved productive performance compared with a negative control group. Significant effect on production parameters could be observed during the trial. Mortality percentage was reduced in both *Bacillus* groups and in both trials.

In one of the sites, the number of animals treated per pen with Enrofluxacin to overcome a severe diarrhea was significantly higher (P>0.05) in those animals fed the control diet than those fed *Bacillus*.

This example thus demonstrates that administration of the *Bacillus* composition of the invention can be used for treating and preventing diseases e.g. by inhibiting pathogens, such as *E. coli* and *Clostridium*, in the animal. The *Bacillus* composition can be fed as a direct-fed microbial or as a feed additive to animal feed. The compositions of the present invention are administered or fed to an animal in an amount effective to decrease the growth of pathogenic bacteria such as Clostridia and *Escherichia coli* in the animal gut.

The animal may be selected from the group consisting of poultry, ruminants, calves, pigs, rabbits, horses, fish and pets. In a preferred embodiment, the animal is a farm animal, which is raised for consumption, such as pigs, or as food-producers, such as broilers and egg-producing chickens.

Methods of administering one or more *Bacillus* strains of the invention to a piglet are also provided. Such methods may include feeding one or more *Bacillus* strains of the invention to a mother of a piglet. The strain(s) may be fed during gestation, lactation, or both. The one or more *Bacillus* strain may also be fed to nursery pigs and to grow-finish pigs.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposited Strains

The *Bacillus* mojavensis strain CHCC 15510 has been deposited at DSMZ (Deutsche Sammlung von Mikroorganismen und Zellkulturen GmbH, Inhoffenstrasse 7B, D-38124 Braunschweig) under the accession number DSM 25839 with a deposit date of Apr. 3, 2012 by Chr. Hansen A/S, Denmark. The deposit has been made under the conditions of the Budapest Treaty on the International Recognition of the Deposit of Microorganisms for the Purposes of Patent Procedure.

The *Bacillus amyloliquefaciens* strain CHCC 15516 has been deposited at DSMZ (Deutsche Sammlung von Mikroorganismen GmbH, Inhoffenstrasse 7B, D-38124 Braunschweig) under the accession number DSM 25840 with a deposit date of Apr. 3, 2012 by Chr. Hansen A/S, Denmark. The deposit has been made under the conditions of the Budapest Treaty on the International Recognition of the Deposit of Microorganisms for the Purposes of Patent Procedure.

The *Bacillus amyloliquefaciens* strain CHCC 15536 has been deposited at DSMZ (Deutsche Sammlung von Mikroorganismen und Zellkulturen GmbH, Inhoffenstrasse 7B, D-38124 Braunschweig) under the accession number DSM 27032 with a deposit date of Mar. 21, 2013 by Chr. Hansen A/S, Denmark. The deposit has been made under the conditions of the Budapest Treaty on the International Recognition of the Deposit of Microorganisms for the Purposes of Patent Procedure.

The *Bacillus amyloliquefaciens* strain CHCC 15539 has been deposited at DSMZ (Deutsche Sammlung von Mikroorganismen und Zellkulturen GmbH, Inhoffenstrasse 7B, D-38124 Braunschweig) under the accession number DSM 27033 with a deposit date of Mar. 21, 2013 by Chr. Hansen A/S, Denmark. The deposit has been made under the conditions of the Budapest Treaty on the International Recognition of the Deposit of Microorganisms for the Purposes of Patent Procedure.

The *Bacillus subtilis* strain CHCC 15541 has been deposited at DSMZ (Deutsche Sammlung von Mikroorganismen und Zellkulturen GmbH, Inhoffenstrasse 7B, D-38124 Braunschweig) under the accession number DSM 25841 with a deposit date of Apr. 3, 2012 by Chr. Hansen A/S, Denmark. The deposit has been made under the conditions of the Budapest Treaty on the International Recognition of the Deposit of Microorganisms for the Purposes of Patent Procedure.

For all of the above-identified deposited microorganisms, the following additional indications apply:

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn Embodiments of the present invention are described below, by way of non-limiting examples.

EXAMPLES

Materials:
Veal Infusion Broth (VIB) (Difco, 234420)
Veal Infusion Broth (VIB) agar (VIB+1.5% Agar bacteriological (Agar no. 1), Oxoid LP0011)
T3 agar plates (per liter: 3 g of tryptone, 2 g of tryptose, 1.5 g of yeast extract, 0.05 M sodium dihydrogen phosphate and 0.005 g of MnCl2 [pH 6.8], and 15 g agar)
Laura-Bertani (LB) broth (g/L: Bacto tryptone 10 (Difco 0123), Yeast extract 5 (Oxoid L21), NaCl 10 (Merck nr. 106404))
Brain Heart Infusion (BHI) Broth (Oxoid CM225)
Brain Heart Infusion (BHI) agar (Oxoid CM375)
Bile salts (Bile extract, porcine; Sigma B8631)
Bioassay dishes (Nunc 240845)
Petri dishes (Procudan 140096, petridish with ribs)
Sporulation medium: % (w/w) 95% water; 1.5% nitrogen source (i.e. yeast); 3% saccharide; 0.06% microminerals; dipotassiumhydrogenphosphate 0.1%.
Physiological saline solution with peptone (0.9% sodium chloride, 1% peptone) FKP
VetMIC Lact-1 & Lact-2 (SVA, Uppsala, Sweden)
ISO-SENSITEST Broth (Oxoid CM0473)

Cultures:
*Bacillus* strains were isolated from feces, soil, food sources and collected from strain bank collections and maintained in VIB with 20% glycerol in MTP master plates at −80° C.
Antibiotics:
Ampicillin (Sigma, A9518-5G)
Vancomycin (Sigma, V1764-250MG)
Gentamicin (Sigma, G1264-50MG)
Kanamycin (Sigma, K1377-1G)
Streptomycin (Sigma, 56501-5G)
Erythromycin (Sigma E-5389)
Clindamycin (Sigma, C2569-10MG)
Tetracycline (Sigma T-7660)
Chloramphenicol (Sigma, C0378-5G)
Pathogens:
*E. coli* 0101 F5 (State Serum Institute, Copenhagen, Denmark)
*E. coli* 0147:K89 F4 (State Serum Institute, Copenhagen, Denmark)
*E. coli* 0149:k91,k88a (NCTC 10650) National Collection of Type Cultures
*E. coli* strains were maintained in LB with 20% glycerol in MTP master plates at −80° C.
*Clostridium perfringens* Type A, DSM 756, was maintained in BHI with 20% glycerol at −80° C.

EXAMPLE 1

Pre-Screening 261 isolates from soil and feces and food sources were subjected to a pre-screening for antibiotic sensitivity, pathogen inhibition, bile resistance and sensitivity to low pH.
1.1 Antibiotic Sensitivity
*Bacillus* strains were added in a volume of 50 µl from MTP master plates into 700 µl VIB in DW plates and incubated at 37° C. and 175 rpm overnight. ISO test samples, supplemented with the antibiotics listed in Table 1 at 2 concentrations and ISO controls without antibiotics were added in MTP plates in a volume of 180 µl. Overnight *Bacillus* cultures were diluted 100-fold and transferred in aliquots of 20 µl to ISO test samples and controls. MTP plates were incubated at 37° C. Optical density (OD) at 620 nm was measured in the inoculum and in MTP test plates after 24 and 48 hours of incubation. Antibiotic sensitivity of bacteria was estimated as percentage of OD in ISO test samples to the OD in ISO controls.
1.2 Screening of *Bacillus* Strains for Pathogen Inhibition
*Bacillus* strains were added in a volume of 50 µl from MTP master plates into 700 µl VIB in DW plates and incubated at 37° C. and 175 rpm overnight.
Before the assay *E. coli* strains were grown in LB overnight at 30° C. *C. perfringens* CHCC14372 was grown in BHI overnight in an anaerobic jar at 37° C.
1.2.1 *E.coli* Inhibition by Agar Spot Test
2 ml of *E. coli* overnight culture was mixed with 200 ml liquid VIB agar at 50° C., and poured into each bioassay dish. The dishes were dried in a sterile bench. Overnight *Bacillus* cultures, 2 µl of each, were spotted onto the surface of the VIB agar mixed with *E. coli* and incubated at 37° C. for 2 days. Radii of clarified inhibition zones round the spots were measured and recorded as "high"—radius more than 2 mm, "medium"—radius between 0.5-2 mm and "low"—radius less than 0.5 mm.
1.2.2 *C. perfringens* Inhibition by Agar Spot Test
VIB agar was poured into the bioassay dishes (200 ml per dish) and dried thoroughly in a sterile bench. Overnight

*Bacillus* cultures, 2 µl of each, were spotted onto the surface of the VIB agar dishes and incubated at 37° C. overnight. *C. perfringens* Type A CHCC14372 was added in a volume of 2 ml to 200 ml liquid BHI agar, mixed and overlaid gently into the bioassay dishes with *Bacillus* spots. The dishes were incubated anaerobically at 37° C. for 1 day. Radii of clarified inhibition zones round the spots were measured and recorded as "high" more than 2 mm, "medium"—between 1-2 mm, "low"—less than 1 mm.

1.2.3 *C. perfringens* Inhibition by Well Diffusion Test 2 ml of *C. perfringens* CHCC14372 overnight culture was mixed with 200 ml liquid BHI agar and poured into each bioassay dish. After solidification, the wells of 10 mm were made in BHI agar with a sterile borer and 80 µl of overnight *Bacillus* cultures were transferred into each well. Dishes were incubated anaerobically at 37° C. for 1 day. Radii of clarified inhibition zones round the wells were measured and recorded as "high"—more than 2 mm, "medium"—between 0.5-2 mm and "low"—less than 0.5 mm.

1.3 Bile Resistance Assay

*Bacillus* strains were added in a volume of 50 µl from MTP master plates into 700 µl VIB in DW plates and incubated at 37° C. and 175 rpm overnight. *Bacillus* overnight cultures in a volume of 50 µl were transferred to 800 µl VIB supplemented with 0.3% bile salts (test samples) and VIB without bile (controls) in DW plates. Plates were incubated at 37° C. and 175 rpm. Optical density at 620 nm ($OD_{620}$) was measured at time 0, 6 and 24 hours in VIB with bile and subtracted from the corresponding $OD_{620}$ values in VIB controls. Cultures were ranked according to the differences in $OD_{620}$ values into groups A (OD<0.1), B (OD=0.1-0.4) and C (OD>0.4). Strains in the group A were considered as most resistant to bile salts. Selected strains should be in group A or B. Results for selected strains are presented in Table 2.

1.4 Sensitivity to Low pH (Simulating Gastric Conditions)

VIB aliquots of 800 µl adjusted to pH4 with 1.0 M hydrochloric acid and VIB controls (pH 7) were distributed in DW plates. *Bacillus* strains were added in a volume of 50 µl from MTP master plates into DW plates and incubated at 37° C. and 175 rpm for 24 hours. Optical density ($OD_{620}$) was measured in 200 µl cell suspensions at time 0 and after 24 hours of incubation. Bacterial growth at pH4 was defined by subtraction of $OD_{620}$ values before incubation from the corresponding values after incubation. Cultures showing increase in $OD_{620}$ of more than 0.1 were considered as resistant to pH4 (indicated with an R in Table 2), while the cultures with values $OD_{620}$ less than 0.1 (no growth or negative values) were considered as sensitive to pH4 (indicated with an S in Table 2).

1.5 Results of Pre-Screening:

Based on the pre-screening test 32 strains were selected for the secondary screening. The selected strains should be sensitive for the described antibiotics and show antimicrobial effect against both *E. coli* and *Clostridium perfringens* and perform reasonably in the other performed tests.

Of the 261 isolates from soil and feces and food sources, 161 isolates were antibiotic resistant in the pre-screening test. Of the 100 isolates that were sensitive to antibiotics 56 has antimicrobial effect against *Clostridium perfringens* and only 22 had effect against both *E. coli* and *Clostridium perfringens*. Of these were 12 isolates from the species *B. amyloliquefaciens*. Other representative strains were from the species *B. subtilis* and *B. mojavensis*. Tables 2 and 3 summarize the results of Chr. Hansen proprietory strains (22 of the 32 strains selected for the secondary screening).

EXAMPLE 2

Secondary Screening

Based upon the results of the primary screening 40 selected isolates and reference strains were tested for inhibition of pathogens by repetition of the agar spot tests and for sporulation. 32 strains were also tested for antibiotic sensitivity by the MIC test.

2.1 Screening of *Bacillus* Strains for Pathogen Inhibition

Before the assay 9 ml of VIB was inoculated with *Bacillus* cultures and incubated at 37° C. and 175 rpm overnight. Concurrently, 9 ml of BHI broth was inoculated with *E. coli* strains, and incubated overnight at 37° C. *Clostridium perfringens* was grown at the same conditions in an anaerobic jar.

2.1.1 Inhibition of *E. coli* by Agar Spot Test:

Overnight cultures of pathogens were added in a volume of 2 ml each into 200 ml liquid VIB agar at 50° C., and poured into each bioassay dish. Dishes were dried in a sterile bench. Overnight *Bacillus* cultures were spotted onto the surface of the VIB agar mixed with pathogens and incubated at 37° C. for 2 days. Radii of the inhibition zones around the spots and spots diameters were recorded.

2.1.2 Inhibition of *C. perfringens* by Agar Spot Test

*Bacillus* cultures were spotted onto the surface of the VIB agar in petri dishes and incubated at 37° C. overnight. *C. perfringens* overnight culture in a volume of 2 ml was mixed with 200 ml liquid BHI agar, and poured into VIB agar with grown *Bacillus* spots. The dishes were incubated anaerobically at 37° C. for 1 day. Radii of clarified inhibition zones round the spots were measured.

2.2 Growth in VIB and in Sporulation Medium

*Bacillus* strains were added in a volume of 50 µl from MTP master plates into 700 µl VIB or sporulation medium in DW plates and incubated at 37° C. and 175 rpm for 24 hours. Bacterial growth was determined by optical density at 620 nm ($OD_{620}$) in 200 µl suspensions. Because of a high turbidity of the sporulation medium and its variation between the wells, $OD_{620}$ values before incubation were subtracted from the $OD_{620}$ values in the corresponding wells after incubation. Cultures showing $OD_{620}$ more that 0.4 were ranked to the group A (high growth) and $OD_{620}$ less than 0.4—to the group B (low growth).

2.3 Sporulation in Sporulation Medium

*Bacillus* strains were added in a volume of 50 µl from MTP master plates into 700 µl VIB in DW plates and incubated at 37° C. and 175 rpm overnight. *Bacillus* overnight cultures in a volume of 50 µl were transferred to 700 µl of a sporulation medium (SM) in DW plates. Plates were incubated at 37° C. and 175 rpm for 3 days. Sporulation was followed microscopically and spore percentage (number of spores in relation to total cells) was determined by visual evaluation after 1 day (24 hours), 2 days (48 hours) and 3 days (72 hours) of incubation.

2.4 Antibiotic Sensitivity Measured by MIC

The strains were analyzed for antibiotic sensitivity by measuring the minimum inhibitory concentration (MIC) for a number of antibiotics. The method used was a broth microdilution method as outlined by the standard of CLSI (Clinical and Laboratory Standards Institute M07-A8 and M45-A2).

A suspension of an over-night growth of the strain to be tested is inoculated in ISO-SENSITEST Broth (Oxoid CM0473) in microtitre plates at an approximate concentration of $10^5$ cfu/ml (colony-forming units/ml) in two-fold serial dilutions of the antibiotic to be tested (total volume 100 µl/well) and incubated aerobically for 20-24 hours at 37° C. The pre-fabricated panels VetMIC Lact-1 & Lact-2 comprising the antibiotics ampicillin, vancomycin, gentamicin, kanamycin, streptomycin, erythromycin, clindamycin, tetracycline, and chloramphenicol can be used. The results are recorded after 24 hours as the lowest concentration of the antibiotic to inhibit visible growth. The test was performed twice as two independent biological replicates.

2.5 Results

Results from the 32 selected strains showed that *Bacillus amyloliquefaciens* had the best combined properties of antibiotic sensitivity, antimicrobial effect and sporulation cf. Table 2. Only data relating to Chr. Hansen proprietary strains (22 of the 32 strains) are included.

TABLE 2

Basic data for selected *Bacillus* strains Source, species by gyrB, growth in VIB and sporulation medium as well as sporulation percentage.

| Strains | Source | Species | Antibiotic Resistance | Growth VIB | S M | Sporulation, % Day 1 | Day 2 | Day 3 |
|---|---|---|---|---|---|---|---|---|
| A | Feces | B. mojavensis | Sensitive | A | B | 5 | 95 | 90 |
| B | Feces | B. amyloliquefaciens | Sensitive | A | A | 10 | 99 | 99 |
| C | Feces | B. subtilis | Sensitive | B | A | 0 | 80 | 95 |
| D | Feces | B. amyloliquefaciens | Sensitive | B | A | 40 | 99 | 99 |
| E | Feces | B. amyloliquefaciens | Sensitive | B | A | 20 | 99 | 99 |
| F | Feces | B. amyloliquefaciens | Sensitive | B | A | 50 | 99 | 99 |
| G | Feces | B. amyloliquefaciens | Sensitive | B | A | 95 | 95 | 95 |
| H | Feces | B. amyloliquefaciens | Sensitive | A | A | 99 | 99 | 99 |
| I | Feces | B. amyloliquefaciens | Sensitive | B | A | 80 | 99 | 99 |
| J | Feces | B. amyloliquefaciens | Sensitive | B | A | 50 | 99 | 99 |
| K | LMG | B. amyloliquefaciens | Sensitive | A | A | 2 | 99 | 99 |
| L | Feces | B. licheniformis | Sensitive | B | A | 90 | 99 | NA |
| M | Soil | B. licheniformis | Resistant | B | A | 0 | 1 | 80 |
| N | Soil | B. megaterium | Resistant | B | A | 0 | 0 | 0 |
| O | Feces | B. subtilis | Sensitive | A | B | 0 | 60 | 10 |
| P | Feces | B. pumilus | Resistant | A | A | 0 | 10 | 99 |
| Q | Feces | B. licheniformis | Resistant | A | A | 0 | 1 | 5 |
| R | Feces | B. licheniformis | Resistant | A | A | 0 | few | 40 |
| S | Feces | B. pumilus | Sensitive | A | A | 0 | 10 | 95 |
| T | Soil | B. megaterium | Resistant | B | A | 0 | 0 | 0 |
| U | Soil | B. licheniformis | Resistant | A | A | 0 | few | 70 |
| V | Feces | B. subtilis | Resistant | A | B | 95 | 99 | 90 |

Strain A = 15510;
Strain B = 15516;
Strain C = 15541;
Strain H = 15536;
Strain I 15539

TABLE 3

Inhibition of *E. coli* and *Clostridium perfringens* (mm) as well as resistance against bile and acid by selected *Bacillus* strains
Strain A = CHCC15510; Strain B = 15516; Strain C = 15541; Strain H = 15536; Strain I = 15539
O149, O147 and O101 are the three *E. coli* swine pathogens mentioned under Pathogens

| Strains | Species | Bile 6 h | 24 h | Acid | E.coli, mm inhibition O149 | O147 | O101 | Cl. perfringens, mm Mm |
|---|---|---|---|---|---|---|---|---|
| A | B. mojavensis | C | A | S | 1.5 | 1.7 | 2.3 | 7 |
| B | B. amyloliquefaciens | A | A | S | 2.5 | 2.3 | 3.5 | 8 |
| C | B. subtilis | A | B | R | 1.8 | 1.5 | 2.7 | 7 |
| D | B. amyloliquefaciens | A | A | R | 2 | 1.7 | 2.5 | 6 |
| E | B. amyloliquefaciens | B | A | S | 3 | 3 | 3.5 | 6 |
| F | B. amyloliquefaciens | B | A | S | 2.5 | 2.5 | 3.3 | 7 |
| G | B. amyloliquefaciens | B | B | R | 2 | 1.7 | 2 | 7 |
| H | B. amyloliquefaciens | A | A | R | 3.5 | 3 | 4.5 | 7 |
| I | B. amyloliquefaciens | B | A | R | 2 | 2 | 2 | 8 |
| J | B. amyloliquefaciens | B | A | S | 2 | 2.5 | 2.5 | 8 |
| K | B. amyloliquefaciens | B | A | S | 0.3 | <1 | 1 | 4 |
| L | B. licheniformis | A | B | S | <1 | <1 | 1.3 | 8 |
| M | B. licheniformis | B | A | S | 0 | 0 | 0 | 4 |
| N | B. megaterium | B | A | S | 0 | 0 | 0 | 0 |
| O | B. subtilis | B | A | S | 1 | <1 | 1.3 | 7 |
| P | B. pumilus | A | A | R | 1 | 0 | 1.7 | 8 |

TABLE 3-continued

Inhibition of *E. coli* and *Clostridium perfringens* (mm) as well as resistance against bile and acid by selected *Bacillus* strains
Strain A = CHCC15510; Strain B = 15516; Strain C = 15541; Strain H = 15536; Strain I = 15539
O149, O147 and O101 are the three *E. coli* swine pathogens mentioned under Pathogens

| Strains | Species | Bile 6 h | Bile 24 h | Acid | E.coli, mm inhibition O149 | E.coli, mm inhibition O147 | E.coli, mm inhibition O101 | Cl. perfringens, mm Mm |
|---|---|---|---|---|---|---|---|---|
| Q | B. licheniformis | B | B | S | 0 | 0 | 0 | 2 |
| R | B. licheniformis | B | B | S | 0 | 0 | 0 | 2 |
| S | B. pumilus | A | A | R | <1 | 0 | <1 | 6 |
| T | B. megaterium | A | A | S | 0 | 0 | 0 | 0 |
| U | B. licheniformis | B | B | S | 0 | 0 | 0 | 3 |
| V | B. subtilis | C | A | S | 2.5 | 1 | 2.5 | 10 |

EXAMPLE 3

Heat Stability 3.1 Method for Heat Stability Test

*Bacillus* strains were grown overnight in VIB at 37° C. and 220 rpm. Overnight cultures were spread on T3 agar plates (100 µl of 105-106 dilutions) and incubated at 37° C. for 1-2 days until sporulation was complete. Spores were scraped from the plates, suspended in FKP solution and incubated at 80° C. for 15 min in order to inactivate vegetative cells. Spore suspensions were placed on ice immediately after heating. Spores preparations were washed twice in FKP, re-suspended in FKP with 20% glycerol and kept at 80° C. before use. Heat resistance of bacterial spores was accessed by holding eppendorf tubes with 500 µl of spore suspensions in FKP (at concentration of approximately 1×106 CFU per ml) at 99.5° C. for 2, 5 and 10 min. CFU counts were determined in dilutions of heated suspensions plated onto VIB agar after incubation at 37° C. overnight.

3.2 Results of Test for Heat Stability

Heat stability data are shown in Table 4.

TABLE 4

Heat stability at 99.5° C. of selected *Bacillus* strains; measured in cfu as reduction after 2, 5 and 10 min in relation to time 0 (log/log)
Strain B = 15516; Strain C = 15541, Strain H = 15536

| Strains | Species | Reduction in cfu after 2 min | 5 min | 10 min |
|---|---|---|---|---|
| B | B. amyloliquefaciens subsp amyloliquefaciens | 0.05 | 0 | 0 |
| C | B. subtilis | 0.25 | 2.5 | 3.8 |
| D | B. amyloliquefaciens/ siamensis related | 0 | 0 | 0.05 |
| E | B. amyloliquefaciens subsp. plantarum | 0.34 | 3.8 | 5.3 |
| F | B. amyloliquefaciens subsp. amyloliquefaciens | 0 | 0 | 0 |
| H | B. amyloliquefaciens subsp. plantarum | 0.19 | 2.5 | 5 |

In general a reduction of less than 2 (log/log) cfu after 2 min in relation to time 0 is appropriate for spores to be included in feed for pelletizing and results below 2 are achieved with common commercial *Bacillus* spores preparations. Thus all strains tested and shown in Table 4 have good heat stability. Some strains also showed good heat stability after 5 and 10 minutes, i.e. strain B and strain F, both *B. amyloliquefaciens* subsp. *amyloliquefaciens*, that showed no cfu reduction.

EXAMPLE 4

Enzyme Production 4.1 Method for Cellulase Assay

*Bacillus* strains were grown in carboxymethyl cellulose (CMC) medium (Abou-Taleb et al. 2009) (per l: 10.0 g carboxymethyl cellulose (C9481), 2.0 g Bacto Tryptone (cat. 211705, Becton Dickinson A/S, Denmark), 4 g $KH_2PO_4$, 4.0 g $Na_2HPO_4$, 0.2 g $MgSO_4.7H_2O$, 0.001 g $CaCl_2$ $2H_2O$, 0.004 g $FeSO_4.7H_2O$, pH 7) at 37° C. and vigorous magnetic agitation for 24 hours. Cellulase production was determined using the EnzChek Cellulase Substrat kit (cat. E33953, Life Technologies) according to the manufacturer's instructions. Shortly, culture supernatants were collected by centrifugation and distributed in MTPs (200 µl per well) in serial dilutions. Standard curves were constructed using cellulase from *Aspergillus niger* (C1184) starting from 2 U $ml^{-1}$. EnzChek substrate solution was added to the culture supernatants in Nunc 96 well Black FluoroNunc plates (cat. 237105, Thermo Fisher Scientific, NUNC Inc.). Fluorescence was recorded at excitation 360 nm/emission 420 nm after 30 min incubation (Enspire 2300 Multilabel Reader, Perkin Elmer Inc.). Cellulase activity was calculated from standard curves in two independent experiments and expressed as means (U $ml^{-1}$).

4.2 Method for Xylanase Assay

*Bacillus* cultures were grown in medium containing beech wood xylan (Cordeiro et al. 2002) (per l: 5.0 g xylan (X4252), 2.0 g Yeast Extract (cat. 288620, Becton Dickinson A/S, Denmark), 5.0 g Bacto Peptone (cat. 211677, Becton Dickinson A/S, Denmark), 0.5 g NaCl, 0.5 g $MgSO_4.7H_2O$, 0.15 g $CaCl_2$ $2H_2O$, pH 7.5) at 37° C. and vigorous magnetic agitation for 24 hours. The xylanase assay was performed with the use of the EnzChek Ultra Xylanase Assay Kit (cat. E33650, Life Technologies) according to the manufacturer's instructions. Briefly, culture supernatants were collected by centrifugation, distributed in MTPs (200 µl per well), in serial dilutions and added xylanase substrate working solution. Fluorescence in culture supernatants was measured at excitation 360 nm/emission 420 nm after incubation for 30 min (Enspire 2300 Multilabel Reader, Perkin Elmer Inc.). *Thermomyces lanuginosis* (X2753) was used as standard enzyme and loaded in MTPs in serial dilutions, starting from 25 mU $ml^{-1}$. Xylanase activity of the *Bacillus* strains was calculated from the standard curves and expressed as means (mU ml$^{-1}$) of two independent assays.

4.3 Method for Protease Assay

Bacillus overnight cultures (grown in VIB at 37° C.) were transferred to a reaction mixture with Fluorescein Isothiocyanate-casein (FITC-C) as substrate (Sigma C3777) and incubated at 37° C. 3 hours. After precipitation the amount of soluble peptides was measured by fluorescence, at excitation 497 nm, emission 515 nm. This assay detects a wide range of proteases (serine, aspartic, cysteine and metalloproteases).

4.4 Methods for Biofilm Production

Bacillus strains were added in VIB (about 10$^7$ CFU ml$^{-1}$), distributed into Polypropylene (PP) MTPs (96 Well Conical Btm PP Plt Natural; NUNC Inc., Denmark) and incubated at 37° C. for 24 hours without shaking. Growth was controlled by measurements of the optical density (OD) at 620 nm. Biofilm formation was assessed by crystal violet staining with as described previously (Auger et al. 2009). Briefly, after washing the wells with distilled water, crystal violet solution of 0.1% (w v$^{-1}$) was added to PP-MTPs and the plates were incubated for 30 min. Then, the washing procedure was repeated and ethanol 96% (v v$^{-1}$) was added to the plates. The absorbance at 570 nm was measured after 15 min incubation (Wallac Victor2 spectrophotometer, Perkin Elmer Inc.). The Bacillus spp. strains were classified as either high (Abs$_{570\,nm}$>2.0), medium (Abs$_{570\,nm}$=1.0-2.0) or low (Abs$_{570\,nm}$<1.0) biofilm producers. The assay was performed twice in duplicates.

4.5. Results for Enzyme Assays

TABLE 5

Enzyme production and Biofilm
(RFU = relative fluorescence unit)
Strain A = 15510; Strain B = 15516; Strain C = 15541;
Strain H = 15536; Strain I = 15539

| Strains | Species | Cellulase, mU/ml | Xylanase, mU/ml | Protease, RFU/OD | Biofilm |
|---|---|---|---|---|---|
| A | B. mojavensis | 1734 | 50 | 142117 | + |
| B | B. amyloliquefaciens subsp. amyloliquefaciens | 67 | 47 | 599919 | + |
| C | B. subtilis | 1037 | 24 | 445091 | + |
| D | B. amyloliquefaciens/siamensis related | 2196 | 70 | 291908 | +++ |
| E | B. amyloliquefaciens subsp. plantarum | 612 | 28 | 381459 | +++ |
| F | B. amyloliquefaciens subsp. amyloliquefaciens | 54 | 57 | 400456 | +++ |
| G | B. amyloliquefaciens subsp. plantarum | 371 | 71 | 453158 | +++ |
| H | B. amyloliquefaciens subsp. plantarum | 631 | 30 | 252377 | ++ |
| I | B. amyloliquefaciens subsp. plantarum | 466 | 121 | 411206 | +++ |
| J | B. amyloliquefaciens subsp. plantarum | 469 | 72 | 421338 | +++ |

The table shows that strains E, G, H, I and J which are all B. amyloliquefaciens subsp. plantarum have high cellulase activity whereas strains B and F which are B. amyloliquefaciens subsp. amyloliquefaciens have low cellulase activity.

EXAMPLE 5

Piglet Trials

Two selected Bacillus strains (Strain B or C) were supplemented to nursery diets to assess their effect on growth performance and mortality of post-weaned piglets. As E. coli is one of the main pathogens in the nursery period with great impact on production parameters and mortality these trials can give information about the effect on E. coli inhibition in the animals. The trials were performed at 2 different sites; site 1 was a research farm and site 2 a university. The trial set up was similar at both sites.

TABLE 6

Overview of sites used in piglet trials

| | Total no. of pigs | No. of replicates | Weighings | Days in trial |
|---|---|---|---|---|
| Site 1 | 576 | 96 | 28, 35, 42, 63 | 35 |
| Site 2 | 720 | 24 | 28, 35, 49, 63 | 35 |

5.1.1 Experimental Set Up at Site 1

The day of weaning, 576 piglets (28 days old) from two consecutive weaning batches (288 piglets each), originating from the experimental farm, were used in the experiment. Piglets were crossbred piglets (ACMC x Pietrain). Selected piglets were healthy with good general aspect and did not receive any vaccination in the nursery phase. The experimental farm was positive to Porcine Reproductive & Respiratory Syndrome (PRRS), but under control, and had some problems of colibacillosis in the post-weaning phase. The piglets were sorted according to body weight and then allocated to 48 pens in both weaning batches (96 pens in total) such that each block of pens contained 6 piglets, 3 entire males and 3 females, of similar body weight in both treatments. The treatments were allocated to the pens of light and heavy piglets by block, so that each treatment was applied to 24 pens of 6 piglets (6 pens per treatment and room; 12 pens per treatment and weaning batch). Bacillus products were added to the feed at 400 g/ton of feed or 1.28*10 7 CFU g/feed.

Pigs were individually weighed at 28 (day 0; weaning day), 35, 42 and 63 days of age to calculate the average daily weight gain (ADWG). Average daily feed intake (ADFI) and feed conversion ratio (FCR) were measured by pen in the same phases (28-35; 35-42; 42-63) and for main periods (prestarter: 28-42 days of age; starter: 42-63 days of age; and total nursery period). Mortality and incidence of pathologies were controlled daily, including registration of individual antibiotic treatments applied.

TABLE 7

Production parameters at site 1

| | Body weight, kg | | 28-42 days of age (14 days in trial) | | | 42-63 days of age | | | Total (28-63 days) | | |
|---|---|---|---|---|---|---|---|---|---|---|---|
| | 28 d | 63 d | ADG | ADFI | FCR | ADG | ADFI | FCR | ADG | ADFI | FCR |
| Control | 7.7 | 20.7 | 179 | 254 | 1.43 | 493 | 697 | 1.42 | 371 | 522 | 1.40 |
| Strain B | 7.7 | 21.1 | 196[A] | 264 | 1.37[A] | 513 | 723[A] | 1.41 | 383 | 535 | 1.40 |
| Strain C | 7.8 | 21.0 | 199[a] | 267[A] | 1.37[A] | 501 | 710 | 1.42 | 380 | 532 | 1.40 |
| SE | 0.150 | 0.254 | 0.007 | 0.006 | 0.024 | 0.010 | 0.010 | 0.008 | 0.007 | 0.007 | 0.009 |

P-values compared to control
[A] $P =< 0.1$;
[a] $=<0.05$)
Strain B = 15516;
Strain C = 15541
SE = Standard Error

5.1.2 Results

Both *Bacillus* strains probiotic products supplemented to nursery diets numerically improved productive performance compared with a negative control group, without showing differences between them. Significant effect on both ADG and FU could be observed in the prestarter phase (28-42 days of age). Mortality percentage was reduced in both *Bacillus* groups (Mortality %: Control (3.47), Strain B (1.39%), Strain C (2.08))

Trial started at weaning at 28 days of age. Animals were individually weighted on days 0 and 7 and group weighted on days 21 and 35 days in trial. Feed disappearance from each hopper was measured throughout the experiment. Average daily feed intake (ADFI), average daily gain (ADG) and feed:gain ratio (FCR) according to the total feed intake were therefore calculated. The health status of piglets was regularly assessed and any abnormal signs or medications given were recorded. Mortality rate and culling percentage were also calculated.

TABLE 8

Production parameters at site 2 least square means,

| | 28-35 days of age | | | 49-63 days of age | | | Total (28-63 days) | | |
|---|---|---|---|---|---|---|---|---|---|
| | ADG | ADFI | FCR | ADG | ADFI | FCR | ADG | ADFI | FCR |
| Control | 73.8 | 157 | 2.26 | 345 | 602 | 1.76 | 227 | 388 | 1.72 |
| Strain B | 80.9 | 174 | 2.26 | 375[A] | 584 | 1.58[A] | 235 | 383 | 1.64 |
| Strain C | 87.1 | 166 | 1.96 | 379 | 586 | 1.60 | 232 | 389 | 1.69 |
| SE | 0.010 | 0.008 | 0.0002 | 0.019 | 0.025 | 0.0001 | 0.0091 | 0.0066 | 0.00065 |

P-values compared to control
[A] $P =< 0.1$)
Strain B = 15516;
Strain C = 15541

5.2.1 Experimental Set Up at Site 2

Just after weaning all the piglets selected were housed in a weaning room of 24 pens with thirty animals per pen. The room is equipped with central heating and forced ventilation with cooling system and completely slatted floors. Each pen it is equipped with a commercial double-sided wet-dry feeder to ensure ad libitum feeding and free water access with a capacity for feeding three animals at the same time. Feed was distributed ad libitum throughout the entire experimental phase.

A total of seven hundred and twenty commercial crossing weanling piglets [Pietrain x (Landrace x Large White)] were used. The animals were obtained from the sows of the same farm on the day of weaning and moved to the experimental facility (without transport). Male and female 26 d-old piglets of 7.0 kg SD=1.64 kg of BW were used. Plastic ear tag identification with the animal's number was used. The animals were distributed into three blocks by initial body weight. Within each block piglets were distributed in pens for a balanced body weight distribution. Therefore, each block consisted of 8 pens of 30 animals to which the experimental diets were randomly assigned.

5.2.2 Results

Both *Bacillus* strains supplemented to nursery diets numerically improved productive performance compared with a negative control group, without showing differences between them. Significant effect on both ADG and FU could be observed in trial periods.

The number of animals treated per pen with Enrofluxacin to overcome a severe diarrhea was significantly higher (P>0.05) in those animals fed the control diet than those fed *Bacillus* during the first week post-weaning. The same results (P<0.05) were observed for the entire experimental period (0 to 35 days post weaning). Mortality percentage was reduced in both *Bacillus* groups (Mortality %: Control (4.17), Strain B (0.04%), Strain C (2.65))

REFERENCES

Barbosa et al., 2005, Screening for *Bacillus* Isolates in the Broiler Gastrointestinal Tract, Applied and Environmental Microbiology, 968-978

Benitez et al., 2011, Antimicrobial Activity of *Bacillus amyloliquefaciens* LBM 5006 is enhanced in the Presence of *Escherichia Coli*, Curr Microbiol 62, 1017-1022

Chaiyawan et al., 2010, Characterization and probiotic properties of *Bacillus* strains isolated from broiler, The Thai Journal of Veterinary Medicine, 40, 2, 207-214

Cutting, S. M. 2011. *Bacillus* probiotics. Food Microbiology 28 (2):214-20.

EFSA 2008. Technical Guidance. Update of antibiotic resistance criteria. The EFSA Journal 732, 9-15

Guo et al, 2006, Screening of *Bacillus* strains as potential probiotics and subsequent confirmation of the in vivo effectiveness of *Bacillus subtilis* MA139 in pigs, Antonie van Leeuwenhoek 90:139-146

Klose et al., 2010. In vitro antagonistic activities of animal intestinal strains against swine-associated pathogens. Vet. Microbiology 144: 515-521.

López, D., and R. Kolter. 2010. Extracellular signals that define distinct and coexisting cell fates in bacillus subtilis. FEMS Microbiol. Rev. 34(2): 134-149.

Spiehs, M. J., G. C. Shurson, and L. J. Johnston. 2008. Effects of two direct-fed microbial on the ability of pigs to resist an infection with *salmonella enterica* serovar *typhimurium*. Journal of Swine Health and Production. 16(1): 27-36.

The invention claimed is:

1. A probiotic animal feed or animal feed premix composition with improved resistance to growth of *Escherichia coli* (*E. coli*) and *Clostridium perfringens*, comprising
  (a) from $10^5$ to $10^{12}$ CFU/g of one or more *Bacillus* strains that exhibit (i) sensitivity for ampicillin, vancomycin, gentamicin, kanamycin, streptomycin, erythromycin, clindamycin, tetracycline and chloramphenicol; (ii) antimicrobial activity against *E. coli* and *Clostridium perfringens*; and (iii) a sporulation percentage of at least 80 when measured after 2 days of incubation, and
  (b) one or more animal feed or animal feed premix ingredients,
  wherein at least one of the one or more *Bacillus* strains is selected from: (a) *Bacillus mojavensis* strain CHCC 15510 deposited with Deutsche Sammlung von Mikroorganismen and Zellkulturen GmbH, Inhoffenstrasse 7B, D-38124 Braunschweig, Germany (DSMZ) under accession number DSM 25839; (b) *Bacillus amyloliquefaciens* strain CHCC 15516 deposited with DSMZ under accession number DSM 25840; (c) *Bacillus amyloliquefaciens* strain CHCC 15536 deposited with DSMZ under accession number DSM 27032; (d) *Bacillus amyloliquefaciens* strain CHCC 15539 deposited with DSMZ under accession number DSM 27033; and (e) *Bacillus subtilis* strain CHCC 15541 deposited with DSMZ under accession number DSM 25841, and
  wherein the one or more *Bacillus* strains are effective to inhibit growth of *E. coli* and *Clostridium perfringens*.

2. The composition according to claim 1, wherein the one or more *Bacillus* strains inhibit growth of *E. coli* as determined by an inhibition zone of at least 1.5 mm when measured by an *E. coli* agar spot test.

3. The composition according to claim 1, wherein the composition comprises two or more of said *Bacillus* strains.

4. The composition according to claim 3, wherein the two or more of said *Bacillus* strains are selected from (a) the *Bacillus mojavensis* strain CHCC 15510 with accession number DSM 25839; (h) the *Bacillus amyloliquefaciens* strain CHCC 15516 with accession number DSM 25840; (c) the *Bacillus amyloliquefaciens* strain CHCC 15536 with accession number DSM 27032; (d) the *Bacillus amyloliquefaciens* strain CHCC 15539 with accession number DSM 27033 and mutants thereof; and (e) the *Bacillus subtilis* strain CHCC 15541 with accession number DSM 25841.

5. The composition according to claim 3, wherein the composition comprises the *Bacillus mojavensis* strain CHCC 15510 with accession number DSM 25839 and the *Bacillus subtilis* strain CHCC 15541 with accession number DSM 25841.

6. The composition according to claim 3, wherein the composition comprises the *Bacillus amyloliquefaciens* strain CHCC 15516 deposited with DSMZ under accession number DSM 25840 and the *Bacillus subtilis* strain CHCC 15541 with accession number DSM 25841.

7. The composition according to claim 3, wherein one of the two or more of said *Bacillus* strains comprises the *Bacillus mojavensis* strain CHCC 15510 with accession number DSM 25839.

8. The composition according to claim 3, wherein one of the two or more of said *Bacillus* strains comprises the *Bacillus amyloliquefaciens* strain CHCC 15516 with accession number DSM 25840.

9. The composition according to claim 3, wherein one of the two or more of said *Bacillus* strains comprises the *Bacillus amyloliquefaciens* strain CHCC 15536 with accession number DSM 27032.

10. The composition according to claim 3, wherein one of the two or more of said *Bacillus* strains comprises the *Bacillus amyloliquefaciens* strain CHCC 15539 with accession number DSM 27033.

11. The composition according to claim 3, wherein one of the two or more of said *Bacillus* strains comprises the *Bacillus subtilis* strain CHCC 15541 with accession number DSM 25841.

12. The composition according to claim 1, wherein the composition comprises three or more of said *Bacillus* strains.

13. The composition according to claim 12, wherein the three or more of said *Bacillus* strains are selected from (a) the *Bacillus mojavensis* strain CHCC 15510 with accession number DSM 25839; (b) the *Bacillus amyloliquefaciens* strain CHCC 15516 with accession number DSM 25840; (c) the *Bacillus amyloliquefaciens* strain CHCC 15536 with accession number DSM 27032; (d) the *Bacillus amyloliquefaciens* strain CHCC 15539 with accession number DSM 27033; and (e) the *Bacillus subtilis* strain CHCC 15541 with accession number DSM 25841.

14. The composition according to claim 1, wherein the composition includes from $10^6$ to $10^{12}$ CFU/g of said one or more *Bacillus* strains.

15. The composition according to claim 1, wherein the composition includes from $10^7$ to $10^{12}$ CFU/g of said one or more *Bacillus* strains.

16. The composition according to claim 1, wherein the one or more animal feed or animal feed premix ingredients are selected from whey, whey permeate, calcium carbonate, limestone, aluminum silicates, and diatomaceous earth.

17. The composition according to claim 1, wherein the composition is an animal feed and the one or more animal feed ingredients comprises feed protein and/or feed carbohydrates.

18. The composition according to claim 1, wherein the composition is an animal feed comprising one or more animal feed ingredients for an animal selected from poultry, ruminants, calves, pigs, rabbits, horses, and fish.

19. A method for producing an animal feed or animal feed premix with improved resistance to growth of *Escherichia coli* (*E. coli*) and *Clostridium perfringens*, comprising
  adding from $10^5$ to $10^{12}$ CFU/g of one or more *Bacillus* strains that exhibit (i) sensitivity to ampicillin, vancomycin, gentamicin, kanamycin, streptomycin, erythromycin, clindamycin, tetracycline and chloramphenicol; (ii) antimicrobial activity against *E. coli* and *Clostridium perfringens*; and (iii) a sporulation percentage of at least 80 when measured after 2 days of incubation, to an animal feed or animal feed premix composition comprising animal feed or animal feed premix ingredients, wherein at least one of the one or more *Bacillus* strains is selected from: (a) *Bacillus mojavensis* strain CHCC 15510 deposited with Deutsche Sammlung von Mikroorganismen und Zellkulturen GmbH, Inhoffenstrasse 7B, D-38124 Braunschweig, Germany (DSMZ) under accession number DSM 25839; (b) *Bacillus amyloliquefaciens* strain CHCC 15516 deposited with DSMZ under accession number DSM 25840; (c) *Bacillus amyloliquefaciens* strain CHCC 15536 deposited with DSMZ under accession number DSM 27032; (d) *Bacillus amyloliquefaciens* strain CHCC 15539 deposited with DSMZ under accession number DSM 27033; and (e) *Bacillus subtilis* strain CHCC 15541 deposited with DSMZ under accession number DSM 25841, wherein the one or more *Bacillus* strains are effective to inhibit growth of *E. coli* and *Clostridium perfringens*.

20. The method according to claim 19, wherein the method comprises adding the *Bacillus amyloliquefaciens* strain CHCC 15516 deposited with DSMZ under accession number DSM 25840 and the *Bacillus subtilis* strain CHCC 15541 with accession number DSM 25841.

\* \* \* \* \*